(12) United States Patent
Golden (10) Patent No.: US 9,173,719 B2
(45) Date of Patent: Nov. 3, 2015

(54) FORCE APPLYING ATTACHMENT, KIT AND METHOD FOR PRE-LOOSENING A TOOTH IN ORDER TO FACILITATE REMOVAL THEREOF

(71) Applicant: Beak and Bumper, LLC, Detroit, MI (US)

(72) Inventor: Richard Golden, Detroit, MI (US)

(73) Assignee: Beak and Bumper, LLC, Detroit, MI (US)

( * ) Notice: Subject to any disclaimer, the term of this patent is extended or adjusted under 35 U.S.C. 154(b) by 0 days.

(21) Appl. No.: 14/075,702

(22) Filed: Nov. 8, 2013

(65) Prior Publication Data

US 2015/0132714 A1    May 14, 2015

(51) Int. Cl.
*A61C 3/00* (2006.01)
*A61C 3/14* (2006.01)

(52) U.S. Cl.
CPC ........................................ *A61C 3/14* (2013.01)

(58) Field of Classification Search
CPC .............. A61C 3/14; A61C 3/16; A61C 3/00; A61C 3/164; A61C 3/162; A61C 3/166; A61C 8/0089
USPC .......... 433/141, 146–153, 165; 81/421–426.5
See application file for complete search history.

(56) References Cited

U.S. PATENT DOCUMENTS

| | | | |
|---|---|---|---|
| 4,261 A | 11/1845 | Baker et al. | |
| 8,351 A | 9/1851 | Burch | |
| 75,716 A | 3/1868 | Woolverton | |
| 97,399 A | 11/1869 | Holmes | |
| 145,058 A | 12/1873 | French | |
| 354,863 A | 12/1886 | Hughes | |
| 390,561 A | 10/1888 | Brown | |
| 478,217 A | 7/1892 | Blake, Sr. | |
| 491,519 A | 2/1893 | Blake, Sr. | |

(Continued)

FOREIGN PATENT DOCUMENTS

| | | |
|---|---|---|
| CA | 2492576 A1 | 7/2006 |
| KR | 200270833 | 4/2002 |
| WO | 2008097954 A1 | 8/2008 |
| WO | 2008097961 A1 | 8/2008 |

OTHER PUBLICATIONS

Bennion, Antique Dental Instruments, 1986, Chapter 2, pp. 29-38, Sotheby's Publications, London.

(Continued)

*Primary Examiner* — Cris L Rodriguez
*Assistant Examiner* — Matthew Nelson
(74) *Attorney, Agent, or Firm* — Dinsmore & Shohl LLP (57) ABSTRACT

The present invention discloses a tool, kit and method for applying loading, torsional/twisting, oscillatory or vibration induced forces to a bond line established between a tooth root surface and an associated bone defined socket within which the tooth is held. Forces are applied typically for a given number of cycles or iterations in order to adequately pre-loosen the tooth from the bone. In a most basic variant, a body is adapted to being engaged by an output portion of a force applying tool. The body includes a pair of tooth engaging portions adapted to being inserted into contact with opposite surfaces of the tooth root surface and opposing surfaces associated with the bone receiving socket. The tool introduces loading forces to the engaging portions, causing the tooth to displace within the socket sufficiently to fracture the bond with the bone, thereby facilitating tooth removal.

3 Claims, 6 Drawing Sheets

(56) References Cited

U.S. PATENT DOCUMENTS

| | | |
|---|---|---|
| 491,932 A | 2/1893 | Whitlock |
| 536,166 A | 3/1895 | Angle |
| 553,718 A | 1/1896 | Monfort |
| 610,840 A | 9/1898 | Angle |
| 617,587 A | 1/1899 | Link |
| 681,224 A | 8/1901 | Link |
| 732,288 A | 6/1903 | Felsch |
| 831,307 A | 9/1906 | Spahn |
| 833,375 A | 10/1906 | Dollar |
| 882,404 A | 3/1908 | Miner |
| 902,570 A | 11/1908 | Ellis |
| 908,056 A | 12/1908 | Whitney et al. |
| 996,030 A | 6/1911 | Parker |
| 1,058,743 A | 4/1913 | Gilbert |
| 1,276,274 A | 8/1918 | Shaffer |
| 1,389,954 A | 9/1921 | Mccombs |
| 1,395,714 A | 11/1921 | Johnson |
| 1,399,265 E | 12/1921 | Lay |
| 1,626,226 A | 4/1927 | Cantor |
| 1,628,499 A | 5/1927 | Joesch |
| 1,674,485 A | 6/1928 | Smith |
| 1,675,815 A | 7/1928 | Miller |
| 1,678,313 A | 7/1928 | Atkinson |
| 1,782,364 A | 11/1930 | Hamilton |
| 1,866,771 A | 7/1932 | Johnson |
| 2,030,798 A | 2/1936 | Krajeski |
| 2,212,801 A | 8/1940 | Torbert |
| D145,058 S | 6/1946 | Lukase et al. |
| 2,428,689 A | 10/1947 | Sykes |
| 2,430,271 A | 11/1947 | Brantley |
| 2,497,254 A | 2/1950 | Brantley |
| 2,504,227 A | 4/1950 | Rubba |
| 2,507,784 A | 5/1950 | Hamel |
| 2,563,920 A | 8/1951 | Christensen |
| 2,592,641 A | 4/1952 | Balderstone |
| 2,698,483 A | 1/1955 | Berkowitz |
| 2,944,341 A | 7/1960 | Lane |
| 3,017,692 A | 1/1962 | Floyd |
| 3,456,349 A | 7/1969 | Heimann |
| 3,468,031 A * | 9/1969 | Mumaw ............ 433/146 |
| 3,473,224 A | 10/1969 | Bergendal |
| 3,644,998 A | 2/1972 | Rubino |
| 3,685,097 A | 8/1972 | Scott et al. |
| 3,834,026 A | 9/1974 | Klein |
| 3,866,324 A | 2/1975 | Walser |
| 3,898,738 A | 8/1975 | Linder |
| 4,014,226 A | 3/1977 | Karamarkovich |
| 4,028,969 A | 6/1977 | Politte |
| 4,031,624 A | 6/1977 | Heimann |
| RE29,889 E | 1/1979 | Klein |
| D253,088 S | 10/1979 | Levin |
| 4,230,454 A | 10/1980 | Lococo |
| 4,353,696 A | 10/1982 | Bridges |
| 4,443,196 A | 4/1984 | Rico |
| 4,457,306 A * | 7/1984 | Borzone ............ 606/1 |
| 4,559,853 A | 12/1985 | Oye |
| 4,609,353 A | 9/1986 | Kline |
| D296,822 S | 7/1988 | Fenton |
| 5,044,954 A | 9/1991 | Lukase et al. |
| 5,057,016 A * | 10/1991 | Lukase et al. ......... 433/160 |
| 5,122,058 A | 6/1992 | Lukase et al. |
| 5,205,734 A | 4/1993 | Marangoni et al. |
| D335,249 S | 5/1993 | Hopkins |
| 5,368,600 A | 11/1994 | Failla et al. |
| D362,293 S | 9/1995 | Formaggioni |
| D370,161 S | 5/1996 | Snyder |
| 5,538,421 A | 7/1996 | Aspel |
| D392,167 S | 3/1998 | Cockrell et al. |
| 5,735,857 A | 4/1998 | Lane |
| 5,755,573 A | 5/1998 | LeBlanc |
| D396,619 S | 8/1998 | Hunter |
| 5,833,460 A | 11/1998 | Maeda |
| 5,996,450 A | 12/1999 | St. John |
| 6,042,379 A | 3/2000 | Rodriguez del Val |
| D426,440 S | 6/2000 | Torres |
| 6,210,161 B1 * | 4/2001 | Montgomery ............ 433/146 |
| 6,280,184 B1 | 8/2001 | Hamilton |
| 6,293,790 B1 | 9/2001 | Hilliard |
| 6,345,983 B1 * | 2/2002 | Godfrey ............ 433/159 |
| 6,579,296 B1 | 6/2003 | Macey |
| D490,288 S | 5/2004 | Griffin |
| 6,745,648 B2 | 6/2004 | Stier |
| 6,790,037 B1 | 9/2004 | Orecchia |
| 6,910,890 B2 | 6/2005 | Golden |
| 6,934,991 B2 | 8/2005 | Kinkade |
| 7,021,932 B2 | 4/2006 | Standish |
| 7,128,575 B1 | 10/2006 | Sohn |
| D543,813 S | 6/2007 | Tutorow |
| D561,899 S | 2/2008 | Golden |
| 7,344,375 B2 | 3/2008 | Mukasa et al. |
| D566,840 S | 4/2008 | Golden |
| D567,376 S | 4/2008 | Golden |
| 7,488,173 B2 | 2/2009 | Bochi |
| 7,575,432 B2 | 8/2009 | Helfenbein |
| 2002/0146665 A1 | 10/2002 | Tamura |
| 2004/0101805 A1 | 5/2004 | Golden |
| 2004/0152044 A1 | 8/2004 | Khan-Sullman |
| 2004/0159194 A1 | 8/2004 | Ting |
| 2005/0008987 A1 * | 1/2005 | Standish ............ 433/153 |
| 2005/0070955 A1 | 3/2005 | Young |
| 2005/0170314 A1 | 8/2005 | Golden |
| 2005/0186536 A1 | 8/2005 | Zepf |
| 2005/0214719 A1 | 9/2005 | Hermann |
| 2006/0166167 A1 | 7/2006 | Syfrig |
| 2007/0275348 A1 * | 11/2007 | Lemon ............ 433/119 |
| 2008/0187885 A1 | 8/2008 | Golden |
| 2008/0248446 A1 * | 10/2008 | Pona ............ 433/159 |
| 2008/0254410 A1 * | 10/2008 | Golden ............ 433/159 |
| 2010/0112514 A1 | 5/2010 | Chen |
| 2010/0112515 A1 | 5/2010 | Chen |
| 2010/0266983 A1 | 10/2010 | Ng et al. |
| 2011/0159459 A1 * | 6/2011 | Darwish et al. ............ 433/118 |
| 2011/0256502 A1 * | 10/2011 | Katz ............ 433/114 |
| 2012/0077147 A1 | 3/2012 | Kalange |
| 2012/0202166 A1 | 8/2012 | Kilcher et al. |
| 2013/0040262 A1 * | 2/2013 | Chun et al. ............ 433/118 |
| 2013/0045459 A1 | 2/2013 | Vale |
| 2014/0023988 A1 * | 1/2014 | Sapian ............ 433/118 |

OTHER PUBLICATIONS

Harris, The Principles and Practice of Dental Surgery, Eight Edition, pp. 361-363, 1863, Lindsay & Blakiston, Philadelphia.
Ring, Dentistry an Illustrated History, Sep. 1985, Abradale Press and Harry N. Abrams, Inc.
Coombs, Eagle Beak molar forceps: evolution and usage, Australian Dental Journal, 1985, pp. 360-363, vol. 30, No. 5.
Instrument Darwinism Sally Dummer traces the evolution of an extraction tool, BDANews, May 2008, p. 22, vol. 21, No. 5.
"A Pictoral History of Dentistry" web page. (Believed to have been offered for sale, publicly used, and/or published prior to the filing date of this application.).
Atkinson, Some early dental extraction instruments including the pelican, bird or axe?, Australian Dental Journal, 2002, pp. 90-93, vol. 47, No. 2.
Hyson, The Dental Key: A Dangerous and Barbarous Instrument, Journal of the History of Dentistry, Nov. 2005, pp. 95-96, vol. 53, No. 3. 0.
Wynbrandt, The Excruciating History of Dentistry: Toothsome Tales & Oral Oddities from Babylon to Braces, 1998, pp. 70-71, St. Martin's Press, New York.
Fillebrown, The Use of the Key, The Dental Cosmos, Feb. 1885, pp. 69-74, vol. 27, No. 2.
Busch, Tooth Keys, Journal of the History of Dentistry, Jul. 2003, pp. 57-59, vol. 51, No. 2.
Harn et al., Unusual Instrument Relationship—Wrench or Turnkey, Journal of the History of Dentistry, Mar. 1996, pp. 25-26, vol. 44 No. 1.
Baker & Riley, Lever operated Toothkey, patented 1845, obtained from "http://dmcd.co.il/antiques/big_he.html".

\* cited by examiner

_Fig-1_

_Fig-2_

_Fig-3_

FORCE APPLYING ATTACHMENT, KIT AND METHOD FOR PRE-LOOSENING A TOOTH IN ORDER TO FACILITATE REMOVAL THEREOF

FIELD OF THE INVENTION

The present invention relates generally to pre-loosening tools, kits and associated methods for facilitating the removal of teeth and root tips. More particularly, the present invention discloses an attachment, kit and method for use with a force applying tool (inclusive of any one or more of alternate linear, rotating and/or vibratory induced forces) used to apply a force to the tooth and/or root surface, typically for a given number of cycles or iterations, in order to adequately pre-loosen the tooth by fracturing a bond line established between the tooth and the alveolar bone or process, which is further defined to include the upper maxillae and lower mandible (tooth socket defining) bones. The root surface of the tooth, so loosened, facilitates ease of subsequent extraction.

BACKGROUND OF THE INVENTION

The prior art is documented with various types of tooth removal tools, such as dental pliers for grasping both sides of the tooth during a removal procedure in which the tooth is bent or twisted. Examples of such devices include the ergonomic tool for a-traumatic tooth extraction set forth in US 2013/0045459 to Vale. Other tooth removal devices include such as depicted in the dental fulcrum wrench of Katz, U.S. Patent Application Publication No. 2011/0256502 and the dental plier device for assisting in removal of upper and lower teeth set forth in Golden, U.S. Pat. No. 6,910,890.

SUMMARY OF THE INVENTION

The present invention discloses an attachment, kit and method of using a power inducing tool for applying an alternating loading, rotating torsional, oscillatory or vibratory inducing force to the tooth root surface. The force can be applied to the embedded portion of the tooth (also termed the root surface), extending below the gum and in contact with the maxillae and mandible bones associated with the alveolar process (further defined as the thickened ridge of bone containing the tooth sockets), leading to the inner most root tip. The application of such forces is typically carried out for a given number of cycles or iterations in order to adequately pre-loosen the tooth to facilitate ease of its subsequent extraction. The various attachments are reconfigurable in a number of variants to assist in breaking a bond line established between the embedded tooth root surface and the associated upper maxillae or lower mandible sockets associated with the alveolar process.

In a most basic variant, the device or attachment includes a body, preferably in the form of an elongate stem and is adapted to being engaged by an output portion of a force applying tool. The body includes a pair of crosswise extending tooth engaging portions adapted to being inserted into contact with opposite surfaces of the tooth and opposing seating surfaces associated the bone receiving socket. A bit portion extending from the body is engaged by collet and clamp portions associated with the tool to facilitate exertion of linear loading forces in bi-directional fashion in order to cause the tooth to displace within the socket sufficiently to fracture the bond between the root surface with the bone, thereby facilitating tooth removal.

In a further variant, the body is reconfigured as a two piece construction including both an outer base component and an inner installed pedestal component, ideally for pre-placement into contact with a tooth to bone interface associated with a rear located molar. The bit portion in this variant is configured into a slip motion inducing component which facilitates both the local generation and introduction of pivotal and translational forces to the engaging portions associated with the rear located molar (and which in instances is known to be curved or pointed posing challenges for establishing effective contact surfaces). Either of the above variants include a selected tooth engaging portion being removed from the body and substituted by an extending pad support such that the attachment is repositioned in a subsequent procedure to further assist in establishing fracture along the tooth to bone bond line.

Also disclosed is a method for fracturing a bond established between the tooth root surface and associated receiving socket defined in the maxillae or mandible bones, this including the steps of providing a body including a pair of tooth engaging portions adapted to being inserted into contact with opposite surfaces of the tooth root surfaces and their respective and opposing seating surfaces associated with the bone receiving socket, communicating an output portion of a force applying tool to the body and generating and transferring at least one of a linear, rotary or vibratory force exerted to the tooth engaging portions in order to cause the tooth to displace within the socket sufficiently to fracture the bond with the bone, facilitating tooth removal. Additional steps include generating and transferring continuous directional forces in alternating bi-directional fashion for a given number of cycles.

Other steps include installing a slip motion component to the body in order to generate each of rotary and linear forces to the tooth engaging portions. Additional method steps include removing a selected tooth engaging portion from the body, attaching a support pad in extending fashion to the body, rearranging a remaining affixed tooth engaging portion in contact with a further location of the tooth, arranging the support pad in contact at or below a gum line associated with an opposite surface of the tooth and rotating the body to further assist in fracturing the bond with the bone.

BRIEF DESCRIPTION OF THE DRAWINGS

Reference will now be made to the attached drawings, when read in combination with the following detailed description, wherein like reference numerals refer to like parts throughout the several views, and in which.

DETAILED DESCRIPTION OF THE PREFERRED EMBODIMENTS

As previously described, the present invention discloses a tool, kit and method for applying an alternating loading and/or rotating force to the tooth root surface, the latter being defined as the embedded portion of the tooth bonded to the maxillae (upper) or mandible (lower) bones associated with the alveolar process and leading to the innermost root tip. The load or force is typically applied for a given number of cycles or iterations in order to adequately pre-loosen the tooth to facilitate ease of subsequent extraction. Reference to the embedded sections of the tooth as generally referenced at 1 in FIG. 3 is understood to include each of a portion 2 projecting above the bone and gum line (known as a crown), as well as a further portion 3 representing an embedded region represented by a boundary 4 which defines a socket or seating pocket established within the maxillae or mandible bone, generically referenced at 5, and within which a root surface of each tooth is anchored.

As further shown, the tooth 1 includes innermost projecting root tips 6, with subsequent reference to the embedded portion of the tooth understood to reference any of the bond line 4 established with any embedded portion 3 of the tooth, notably its root surface 3 and/or its innermost associated root tip 6. The kit and method associated with the various types of attachments as set forth herein is further understood to provide the ability to work in situations where most or all of a projecting (crown) portion 2 of a given tooth has been broken off, and where only the root surface 3, root tip 6 and/or some remaining embedded portion 3 of the tooth may remain.

Figures 1, 2:
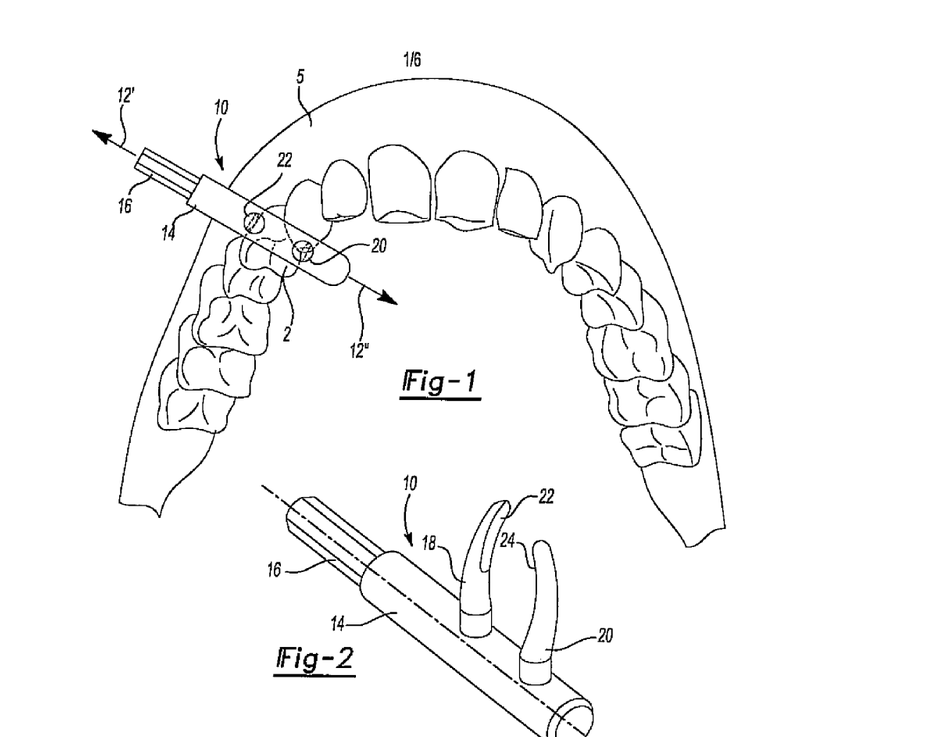
FIG. 1 is an operational view of the tool attachment according to a first variant applying loading forces in series to opposite sides of a selected tooth and in an effort to loosening a bond established between the root surface of the tooth and bone in order to facilitate subsequent tooth removal.
FIG. 2 is an illustration in perspective of the attachment in FIG. 1 depicting an elongate body incorporating a linear driving power tool receiving bit portion, a pair of tooth surface engaging/loading portions extending in crosswise and spaced apart fashion from the body.
Figure 3:
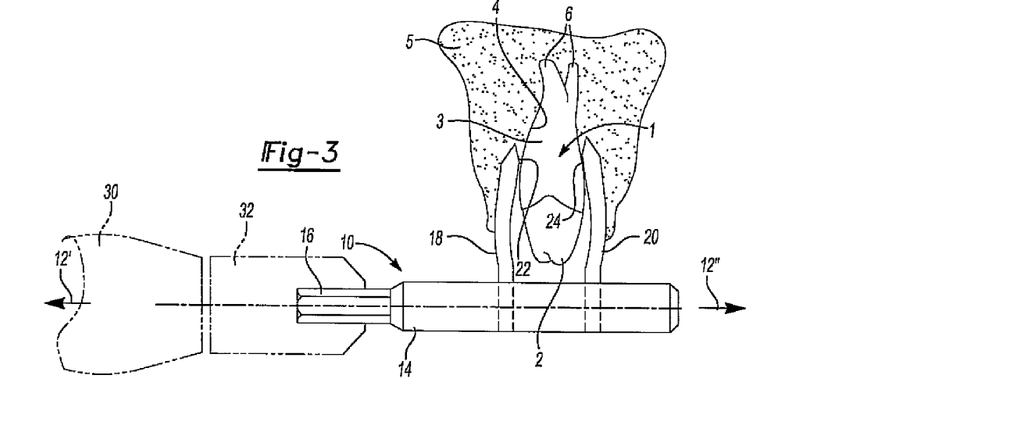
FIG. 3 is a further operational view in plan cutaway and which depicts the tooth loading portions in contact with oppose opposite embedded edges of the tooth root surface, proximate the root tip and along the Alveolar bone line interface.

Referring to FIG. 1, an operational view of the tool or attachment, generally depicted at 10 according to a first variant and which is applied or engaged with a selected tooth, such as further depicted at 2 in FIG. 3. As will be further described, the tool or attachment 10 is capable of being acted upon by a suitable power or force applying tool, such as generally represented at 30 in FIG. 3 and including without limitation such as an impacting hammer or other appropriately designed power tool which is constructed or modified for medical use and which is capable of delivering either one or more of a constant loading force, a torsional (twisting) force, an oscillating force or a vibratory force, for example this in order to transfer loading forces in bi-directionally (see arrows 12' and 12"), either in a series of forces or in an alternating fashion, to opposite sides of the selected tooth, and in an effort to loosen or fracture the bond (see again at 4 in FIG. 3) established between the embedded root surface 3 leading to the inner most root tips 6 with the socket defined in the bone 5, the objective of which is to break the bond line holding the tooth root surface to the bone and to facilitate subsequent tooth removal. It is further understood that the quantum of force applied in either direction 12' or 12", while not specifically articulated, is adequate to break the bond line between the tooth root surface and bone and can vary from patient to patient.

FIG. 2 is an illustration in perspective of the tool 10 depicted in FIG. 1 and which, in the illustrated variant, exhibits an elongate stem-shaped body 14 incorporating a linear driving power tool receiving bit portion 16. As is shown, the bit portion 16 is depicted in linear extending fashion relative to a proximal end of the stem shaped body 14, however it is understood that the bit can be reconfigured with other shapes or structures (such as for example, is subsequently shown in FIG. 18) so that it extends crosswise or in some other orientation relative to the stem shaped body 14.

A pair of tooth surface engaging/loading portions are depicted at 18 and 20 extending in a crosswise and spaced apart fashion from the elongate stem shaped body 14. The engaging portions 18 and 20 in the illustrated variant each exhibit a generally elongated and inwardly opposing curved profile, see at 22 and 24, respectively. As further depicted in FIGS. 6 and 7, a modification 14' of the stem shaped body can include both or a selected one of the tooth engaging portions 20 (typically the most distal one from the bit portion 16) having a frictional or otherwise removable bottom portion 26 which is resistively seated within an aperture 28 defined by an enclosed and depth extending perimeter in the stem shaped body 14', such that the selected tooth engaging portion 20 is capable of being readily detachable from the stem shaped body 14'.

Additional variants envision either or both engaging portions being removable from the stem shaped boy and, to this end, a series of apertures 28 can be formed along the stem in spaced apart fashion to facilitate repositioning of the engaging portions 18 and 20.

The engaging portions 18 and 20 are also capable of being redesigned or modified, such as to include different thicknesses, lengths and contours as well as having sharpened tips to facilitate embedding into the root surface to bone bond line. It is further envisioned that the engaging portions can be provided in kit form and, in combination with an apertured pattern of an associated stem 14, can be quickly configured by the dental professional to achieve a desired engagement profile and separation distance in order to provide cusomized fit and functionality with each patient's oral dimensions. Alternately, it is also envisioned that the attachments can be provided with both the engagement portions integrally formed with the stem, multiple attachments being provided with each having a different separation distance between the engagement portions in another kit variant.

Without limitation, the attachment 10, as well as that associated with any of the subsequently described embodiments, can be constructed of any material not limited to a durable metal or impact resistant plastic. As will be further described, the attachments (or various insert portions associated therewith) can also be constructed of an inexpensive throwaway component or can be produced of higher quality and medical grade steel which can be washed and sanitized in between uses.

Referring again to FIG. 3, a further operational view is shown in plan cutaway and which depicts the tooth loading/engaging portions 18 and 20 in contact with opposite sides of the tooth and the embedded edges of the embedded root surface 3 of the tooth, for example, as shown. The force applying tool is again generally depicted in phantom at 30 and can include any type of electric, pneumatic, hydraulic (even manual) style tool which is capable of imparting any desired linear, rotary, eccentric or vibratory induced force to the tool or attachment 10. This can further include the tool being reconfigured or adapted to provide a variety of different forces, either individually or in alternating fashion. With particular respect to FIG. 3 the tool 30 applies only linear pushing and pulling forces to the tooth once the engaging portions are positioned as shown and regardless of whether the tool 30 also provides (independently) a rotating output.

Accordingly, the invention contemplates the provision of a tool which can introduce any one or more directed forces in consecutive or combined fashion. For example, in one instance using a force applying tool for providing an initial vibratory force to assist in wedging the engaging portions 18 and 20 between the root surface and Alveolar bone bond line following that positioning of portions 18/20 relative to a tooth, loading forces (linear or torsional) can be applied in either alternate or consecutive fashion. In this regard, the present invention further envisions modifying a suitable medically purposed power tool, such as a drill or impact hammer, in order to provide the necessary force delivery features.

Proceeding from the above description, the force delivery tool 30 depicted in non-limiting fashion further exhibits an engaging chuck and/or collet 32, such as which engages or clamps to the projecting bit 16 and, in the illustrated variant, is configured to deliver a continuous loading force in each of two directions (see again bi-directional arrow 12 in FIG. 2). Without limitation, it is further understood that the tool can be redesigned in a number of different configurations and further that the collet/clamp design can be substituted with a socket or other engagement structure dependent upon the nature and direction of the force to be applied to the attachment 10.

Figure 4:
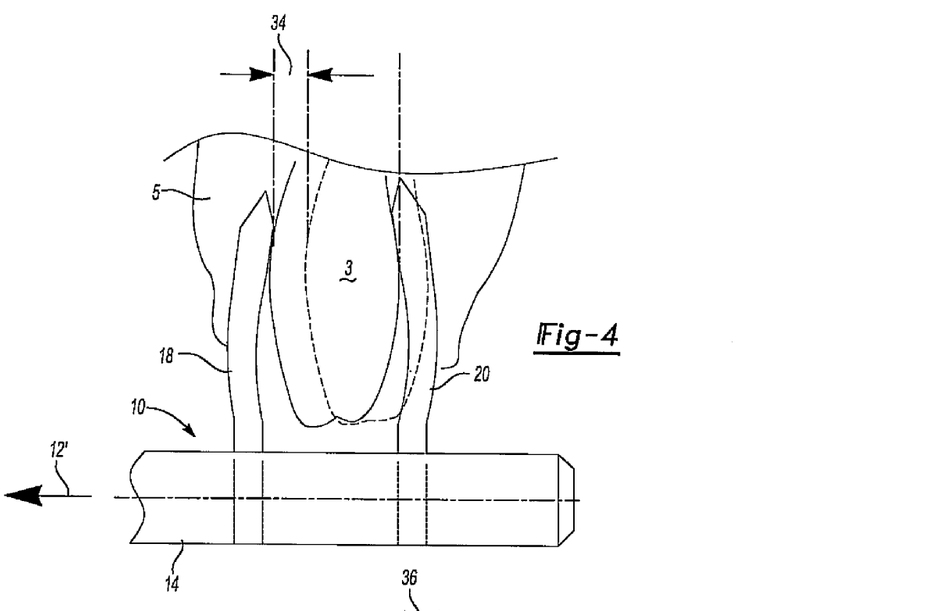
FIG. 4 is an enlarged partial plan view taken from FIG. 3 and illustrating a first directional loading force applied by the tool to the tooth.
Figure 5:
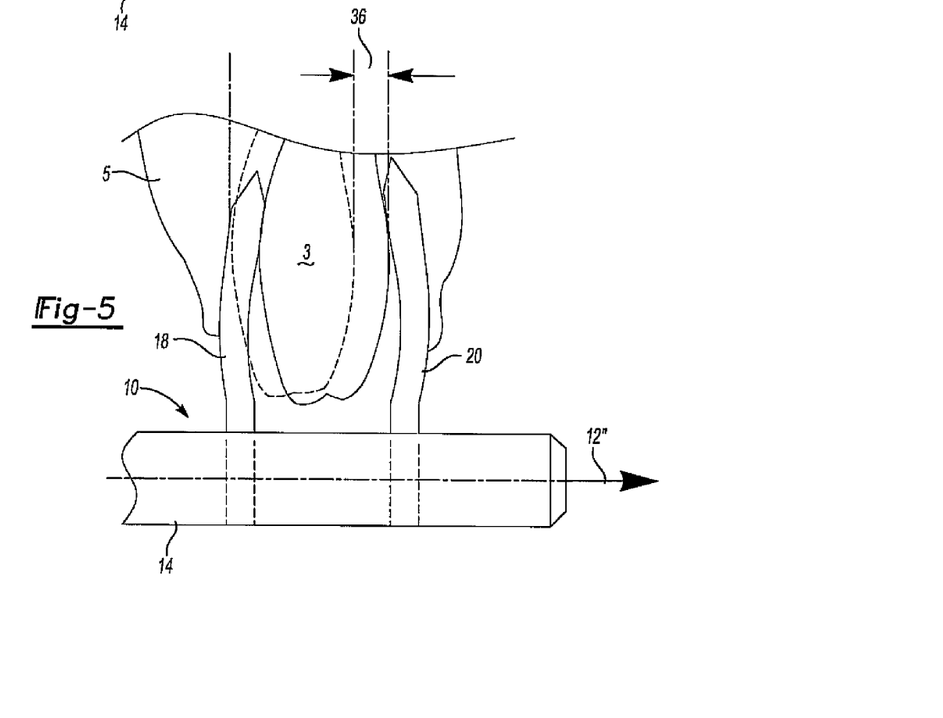
FIG. 5 is a substantially identical illustration to FIG. 4 and illustrating a second and opposite directional loading force applied to the tooth in either of a cyclical or vibratory fashion and resulting in the breaking of a bond line established between the tooth root surface with the alveolar bone.

FIG. 4 is an enlarged partial plan view taken from FIG. 3 and illustrating a first directional loading force 12' applied by the tool 30 and supported attachment to the tooth root surface 3, with FIG. 5 illustrating a second and opposite directional loading force 12" applied to the tooth in alternate loading or vibratory fashion. Among the objectives of applying the loading force to the tooth/bone interface is the release an enzyme which is known to cause separation of the tooth to bone interface, resulting in the breaking of a bond line established between the tooth and root surface (extending to the innermost root tip) with the bone.

As further shown in FIGS. 4 and 5, the use of such forces causes the tooth 2 to displace initially in a first direction 34 (FIG. 4) and then successively in a second opposite direction 36 (FIG. 5). The separation distances associated with tooth displacement can vary but may be within a general range of about 0.5 mm to about 3 mm, and preferably about 1 mm in each direction.

It is also envisioned, again without limitation, that one loosening protocol contemplates applying alternating/cyclical loading forces can be applied for such as 30 seconds in each direction, with adequate loosening of the tooth occurring within as little as 2-3 minutes. Additional protocols include providing an initial loading cycle for a given time interval (e.g. 30 seconds in each direction), with any number of succeeding loading cycles for reduced time intervals (e.g. such as 20 seconds or less in each direction).

Figures 6, 7, 8:
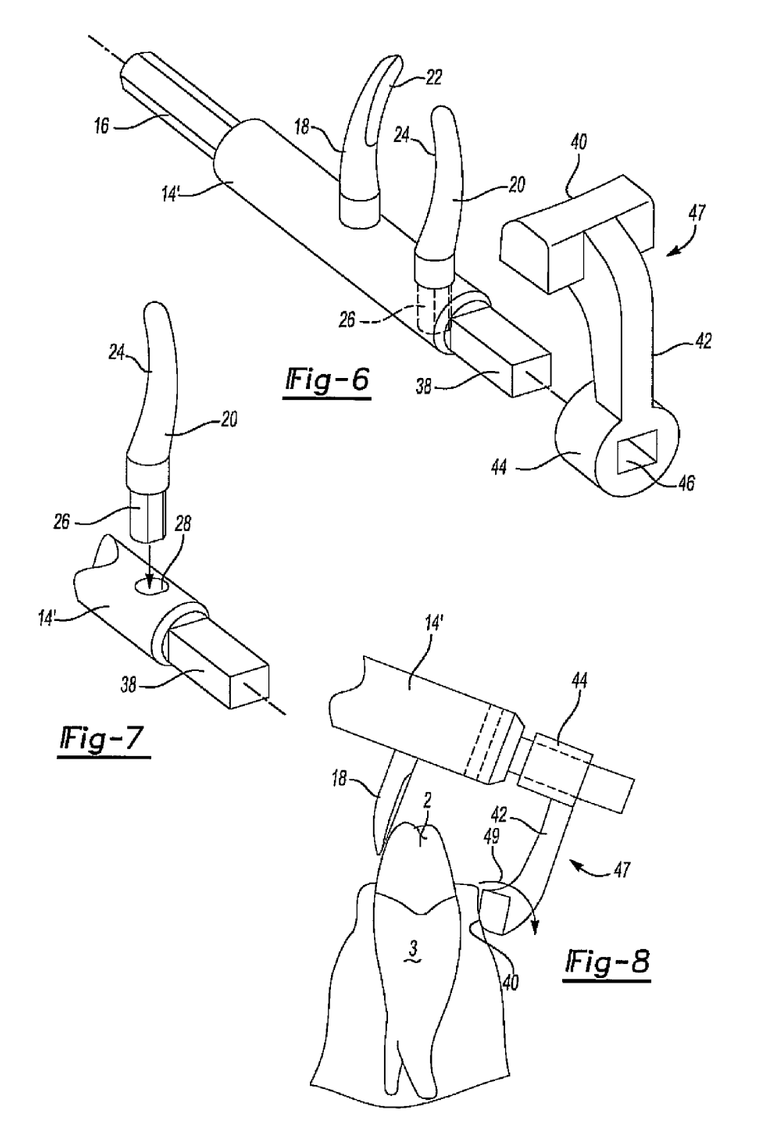
FIG. 6 is an illustration similar to that previously shown in FIG. 2 and depicting either a modification or reconfiguration attachment associated with an extending edge of the tool attachment and which permits attachment of a pad support for engaging a gum line surface proximate the tooth.
FIG. 7 is an enlarged partial illustration taken from FIG. 6 and illustrating detachability of a selected (outer spaced) tooth surface engaging portion as well as an end extending bit receiving portion to which is secured the pad support.
FIG. 8 is a succeeding operational view of the reconfigured tool of FIGS. 6-7 in engagement with a (pre-loosened) tooth to facilitate either of additional loosening or eventual tooth removal.

FIG. 6 is an illustration similar to that previously shown in FIG. 2 and depicting either a modification or reconfiguration associated with an extending end of the tool attachment stem 14', in the form of a distal end rectangular projection 38 which permits attachment of a pad support 47 for applying below a gum line surface (see FIG. 8) proximate the tooth 2. The pad support 47, as shown, includes a width extending support portion 40, a surface of which is configured to apply along the bone below the gum line proximate the tooth root surface as shown in FIG. 8.

Figure 18:
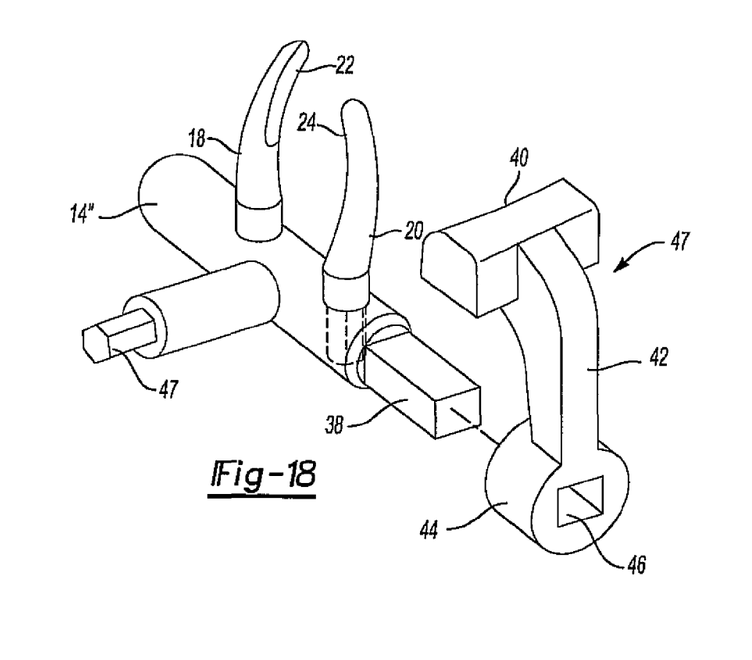
FIG. 18 is an illustration of a further revised variant of the tool comparable to FIG. 2 and illustrating a 90° offset bit engaging portion as well as a yet further variant of attachable pad support, such as facilitating engagement of an upper tooth.

As also depicted in FIG. 18, the support portion 40 is supported at an extending end of a neck 42 which communicates with an interconnecting base 44. A rectangular shaped aperture 46 extends through the base 44 such that the pad support 47 is installed over the distal end projection 38 as shown in FIG. 6 and so that, upon detachment of the selected tooth engaging portion 20, is capable of being repositioned in the manner depicted in FIG. 8 for facilitating either additional loosening or eventual tooth removal by rotation about support 40 as shown by arrow 49, such as in combination with the initial bond line breakage protocol depicted in FIGS. 4-5.

Figures 9, 10, 12:
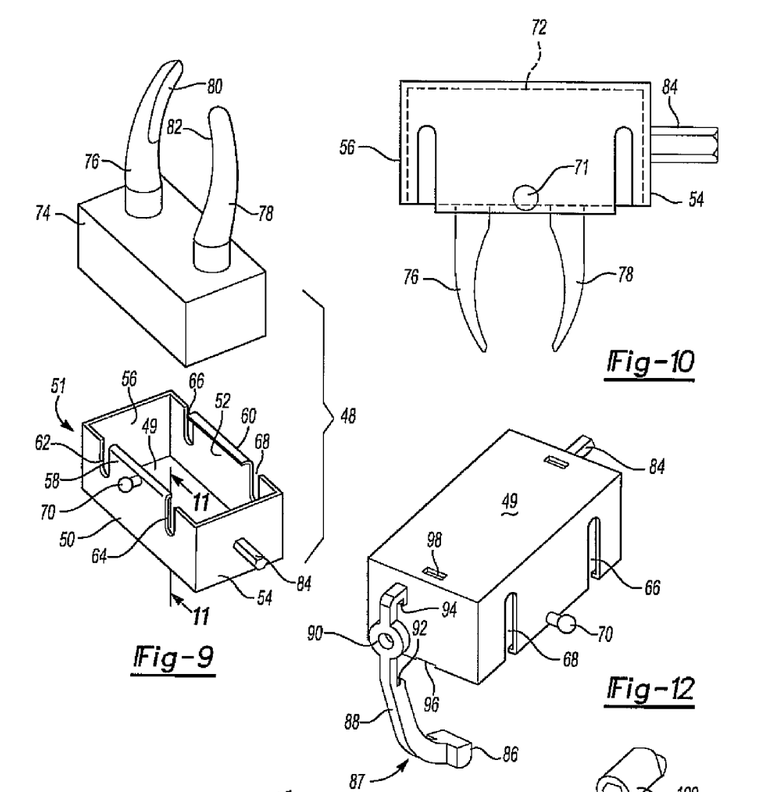
FIG. 9 is an exploded view of a multi-piece tool according to a further embodiment incorporating self-contained and locally induced loading forces such as for use with rear located molars not conveniently accessible by an external force applying tool.
FIG. 10 is an assembled side plan view of the tool of FIG. 9 and depicting in phantom a boundary of a rectangular shaped pedestal associated with an inner component relative to an outer and matching rectangular recess associated with a force inducing base component.
FIG. 12 is an assembled perspective of the tool according to FIG. 9 in a reconfigured variant and which illustrates a pad support attached to an edge of the outer base component in a reconfiguration.

Proceeding to FIGS. 9-13, a series of illustrations are depicted of a multi-piece attachment kit, generally at 48 in FIG. 9, according to a further embodiment incorporating self-contained and locally induced loading forces such as for use with rear located molars not conveniently accessible by an external force applying tool. As best shown in FIG. 9, a base component 51 is provided and exhibits a rectangular and three-dimensional shape with a bottom 49 from which extends sides 50 and 52 and interconnecting ends 54 and 56, which collectively define an open accessible interior.

As further shown, the base component 51 is typically constructed of a plastic or other sufficiently deformable material and, according to the non-limiting example depicted, includes centrally located, upper extending portions 58 and 60 associated with the sides 50 and 52. The upper extending portions 58 and 60 as shown include uppermost and inwardly curled edges and which are partially separated from the top edges by pairs of inner extending and slot shaped edges referenced at 62 & 64 and 66 & 68 which define horizontally spaced and vertical directed channels extending downwardly from top edge locations of the base component 51.

Pull tabs (see at 70 for selected upper portion 58 and further at 71 in FIG. 10 for opposite upper portion 60) are provided to assist in outwardly deflecting the sides to facilitate seating insertion of a likewise rectangular shaped pedestal component 74 installable within the base component. As with the preceding embodiment, a pair of tooth engaging portions 76 and 78 with inner opposing engaging surfaces 80 and 82 are provided and which are adapted to being inserted into contact with opposite surfaces of the tooth (see FIG. 3) and opposing seating surfaces associated the bone receiving socket. Also depicted at 84 is a bit portion projecting from selected end 54 of the base component 51, it again being understood that the bit portion can be repositioned as desired for maximum accessibility of the output drive portion of the powered or force applying tool.

The pedestal component with tooth engaging portions can be provided in varying sizes, such as with the tooth engaging portions (also termed pillars) which are incrementally spaced apart to ensure a maximum degree of fit in both covering the crown of the tooth and applying against the opposite sides of the root surface in contact with the bone as shown in FIG. 3, and so as to be selectively and alternately seated within the base component in the manner depicted. It is further understood that the inserts, including the pedestal component 74 and different tooth engaging portions, can be provided in multiple kit form with varying dimensions in the size or spacing of the tooth engaging portions and can further be either reusable or disposable.

Figure 11:
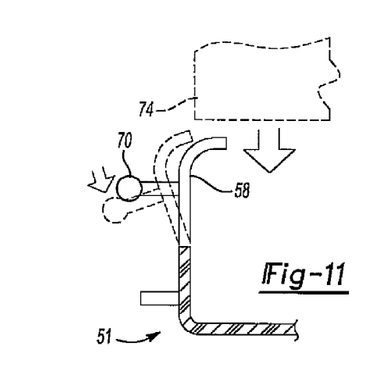
FIG. 11 is a partial side cutaway depicting a non-limiting construction of the outer base to facilitate outward deflection for installing and seating therein the inner pedestal.

FIG. 10 is an assembled side plan view of the tool of FIG. 9 and depicting in phantom a boundary of a rectangular shaped pedestal (see rectangular edge again depicted in phantom at 72) associated with an inner component relative to an outer and matching rectangular recess associated with a force inducing base component. FIG. 11 is a partial side cutaway depicting a non-limiting construction of the outer base to facilitate outward deflection for installing and seating therein the inner pedestal 74 in the manner previously described.

With further reference to FIG. 12, an assembled perspective of the tool according to FIG. 9 is shown in a reconfigured variant and which illustrates another variation of a pad support 87 (as compared to that shown at 40 in FIG. 6) and which is attached to an edge of the outer base component in a reconfiguration thereof. As in the preceding embodiment, the pad support includes a width extending support edge 86 mounted at an end of an extending neck 88.

Figure 13:
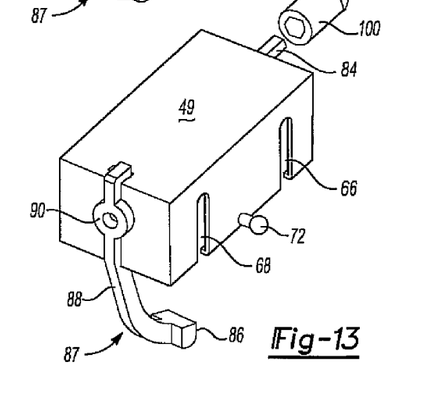
FIG. 13 is a similar perspective as compared to FIG. 12 illustrating a socket attachment arranged in communication a force transferring bit portion associated with the outer base component.

A base mounting portion 90 of the pad support 87 includes a pair of opposing and inner spaced engagement edges 92 and 94 (as shown in exploded fashion in FIG. 12) and which, resistively snap engage within slots 96 and 98 in the associated end of the base component 51 so as to mount the pad support 87 in the manner shown in succeeding FIG. 13. As in the preceding variants, a selected one of the tooth engaging portions 76/78 can be removable concurrent with the installation of the pad support and so that, following an initial loosening step in which the bone line between the opposite sides of the tooth and bone is initially fractured, the attachment can be repurposed with the removal of the selected loosening portion/pillar and the attachment of the extending support pad in order to assist in further separating and removing the tooth or associated root tip (see as again procedurally accomplished in preceding illustration of FIG. 8).

FIG. 13 is a similar perspective as compared to FIG. 12 and also illustrates a socket attachment 100 extending from a power or other force loading tool (not shown in this variant) and which is arranged in communication the force transferring bit portion 84 associated with the outer base component. As with the embodiment of FIG. 1, the power tool can be specially configured to provide a linear loading force to the attachment, and in addition to providing any other rotational or vibratory induced force.

Figure 14:
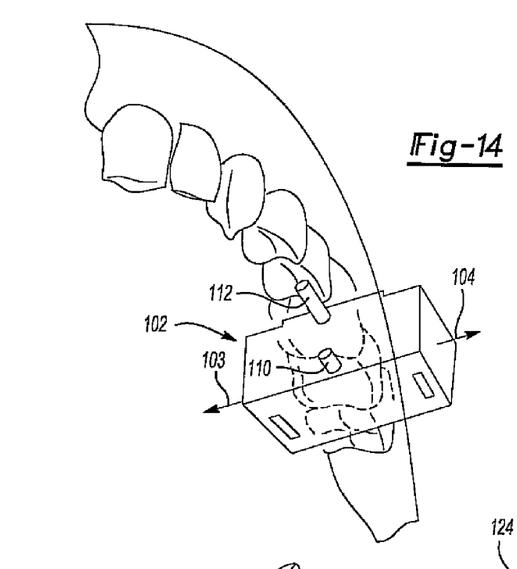
FIG. 14 is an operational view of a further variant of the tool similar to FIG. 9 and depicting a 90° offset engagement configuration with a rear located molar.

FIG. 14 is an operational view of a further variant of tool, generally at 102, similar to FIG. 9 and depicting a 90° offset engagement configuration of an engaging bit portion (see also slip motion inducing component in FIG. 15) for generating linear opposing forces 103 and 104 upon a rear located molar. In one non-limiting variant, the attachment is pre-assembled and press-fit into place along the opposite sides of the molar, prior to attachment of the socket, collet/clamp or other force output component associated with the powered or loading tool.

Figure 15:
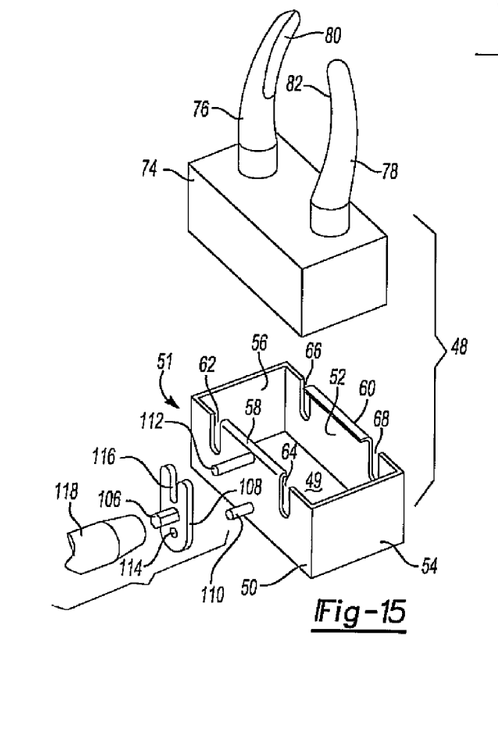
FIG. 15 is an exploded view of the revised variant of FIG. 14 and illustrating a slip motion inducing component incorporated into a redesigned outer base for assisting in generating localized and self-contained loading forces applied to the inner seating pedestal and the tooth engaging portions extending therefrom.

Proceeding to FIG. 15, an exploded view is provided of the revised variant 102 of FIG. 14 and illustrating a slip motion inducing component incorporated into a redesigned outer base for assisting in generating localized and self-contained loading forces applied to the inner seating pedestal and the tooth engaging portions extending therefrom. Specifically, the slip motion feature assists in creating necessary forces within the attachment by rotary input from the power output tool, directly into the tooth to bone line interface.

Figure 16:
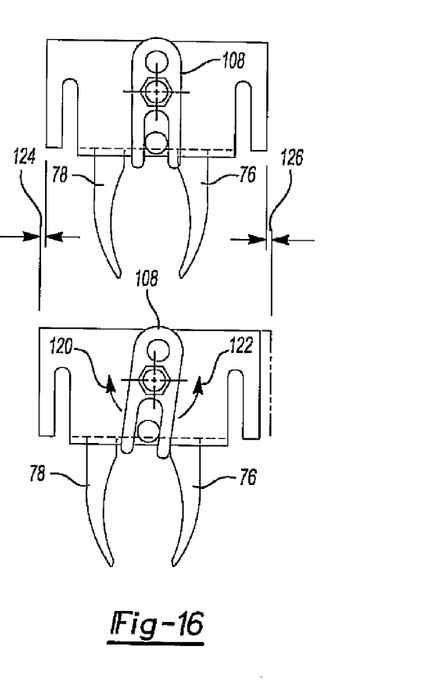
FIG. 16 illustrates in plan view the assembled tool of FIG. 14 with slip motion inducing component in each of first and second force inducing/transferring positions.

As further best depicted in each of FIGS. 15 and 16, a reconfiguration of the bit, at 106, is integrally formed with the motion-inducing component, at 108. Additional features include a pair of spaced apart posts 110 and 112 projecting from the base component (otherwise identically configured to that shown in FIG. 9). A first of the posts 110 seats through an aperture 114 defined adjacent the bottom of the slip motion-inducing component 108, the other of the posts 112 will fit into and be received by an upwardly opening slot 116 in component 108 to produce the application of a combined pivotal and translational forces derived from the motion inducing component.

A socket attachment 118 is provided from any type of rotary or oscillatory force delivery tool (such as a hand held and elongate impact hammer or drill) in order to introduce a combined rotary and translating force to the slip motion component 108 in each of first and second force inducing/transferring positions (see FIG. 16). In this fashion, eccentric and/or oscillatory directional forces are created (see arrows 120/122 in FIG. 16) and result in back-and-forth lateral force shifting of the attachment representative of the bond line breakage of the tooth/molar root surface relative to the bone, and as further depicted at 124 and 126. Without limitation, the slip motion component described herein can be reconfigured or substituted by other structure to assist in localized force generation (from a power input as depicted such as by rotary bit 118) and in order to assist in establishing a necessary fracture force at the bond line between the tooth root surface.

Figure 17:
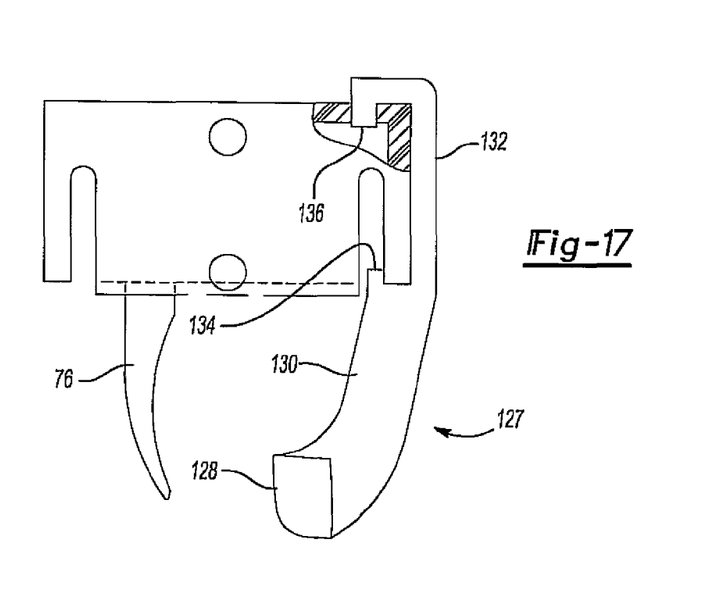
FIG. 17 is a side plan view in partial cutaway of the tool of FIG. 14 and depicting a further variant of attachable pad support as well as detachable tooth engaging portion.

Proceeding to FIG. 17, a side plan view in partial cutaway is shown of the tool of FIG. 14 and depicting a further variant of attachable pad support 127, this being largely similar to that depicted at 86-90 in FIG. 13 and again including a width extending support edge 128, mounting neck 130 and base with engagement edges 134 and 136 spaced in an inner opposing fashion. Selected tooth engagement portion 78 is also removed in FIG. 17 and, with the attachment of the pad support, permits the attachment to be repurposed in the manner similar to that previously described and as shown in FIG. 8.

A method is also disclosed for fracturing a bond line established between a tooth root surface and a bone receiving socket is also disclosed and which includes the steps of providing a body including a pair of tooth engaging portions adapted to being inserted into contact with opposite surfaces of the tooth root surfaces and opposing seating surfaces associated with the bone receiving socket, communicating an output portion of a force applying tool to the body and generating and transferring at least one of a linear, rotary or vibratory force exerted to the tooth engaging portions in order to cause the tooth to displace within the socket sufficiently to fracture the bond with the bone, facilitating tooth removal.

Additional steps include communicating an output portion of the force-applying tool to a bit portion extending from the body, as well as introducing a continuous directional force in alternating bi-directional fashion for a given number of cycles. Additional steps include installing a slip motion component to the body in order to generate each of rotary and linear forces to the tooth engaging portions.

Other steps include removing a selected tooth engaging portion from the body, attaching a support pad in extending fashion to the body, rearranging a remaining affixed tooth engaging portion in contact with a further location of the tooth, arranging the support pad in contact at or below a gum line associated with an opposite surface of the tooth and rotating or levering the body to further assist in fracturing the bond with the bone.

Having described my invention, other and additional preferred embodiments will become apparent to those skilled in the art to which it pertains, and without deviating from the scope of the appended claims.

I claim:

1. An attachment in use with a force applying tool for fracturing a bond established between a tooth root surface and a receiving socket defined in a bone, said attachment comprising:
    a body adapted to being engaged by an output portion of the force applying tool;
    said body further including a pair of outwardly extending, spaced apart tooth engaging portions adapted to being inserted into contact with opposite sides of the tooth root surface and the bone within which the tooth is held;
    said body further having an elongate stem, said tooth engaging portions extending from said elongate stem, at least a selected one of said tooth engaging portions being removably engaged within an aperture defined in said elongate stem;
    a support pad mounted atop a neck and interconnecting base which is engageable with an axially extending end of said elongate stem opposite a bit portion engaged to the force applying tool;
    said extending end of said elongate stem is in the form of a rectangular projection, said base of said support pad having a rectangular recess adapted to receive said rectangular projection in order to mount said support pad in crosswise extending fashion relative to the other selected and affixed tooth engaging portion following removal of the removably engaged tooth engaging portion;
    so that tool introduced loading forces will be imparted to said engaging portions and to the tooth, thereby causing the tooth to displace within the socket sufficient to fracture the bond between the root surface and bone, facilitating tooth removal.

2. An attachment in use with a force applying tool for fracturing a bond established between a root surface of a tooth and a receiving socket defined in a bone and outer gum surface, said attachment comprising:
    an elongated body having a bit portion end adapted to being engaged by an output portion of the force applying tool, said body having a distal and polygonal cross sectional shaped end;
    a pair of tooth engaging portions extending from intermediate locations of said body and adapted to being inserted into contact with opposite sides of the tooth root surface and the bone within which the tooth is held in a first loosening condition, a selected one of said tooth engaging portions being removable from said body in a second removal condition;
    tool introduced loading forces being imparted to said tooth engaging portions in the first condition, causing the tooth to displace within the socket sufficient to fracture the bond between the root surface and bone; and
    a support pad mounted atop a neck, said neck terminating in an interconnecting base with a through aperture for receiving said second end of said body and in order to engage said support pad to said body in the second condition, said other selected one of said tooth engaging portions being applied against a surface of the tooth concurrent with said pad adapted to being applied to the gum surface such that rotation of said body dislodges the tooth.

3. A kit for fracturing a bond established between a root surface of a tooth and a receiving socket defined in a bone and outer gum surface, said kit comprising:
    a power tool delivering a loading force to a collet end;
    an elongated stem shaped body having a bit portion end adapted to being engaged within said collet;
    a pair of tooth engaging portions extending from intermediate locations of said body and adapted to being inserted into contact with opposite sides of the tooth root surface and the bone within which the tooth is held;
    the loading forces being imparted to said tooth engaging portions, causing the tooth to displace within the socket sufficient to fracture the bond between the root surface and bone in a first tooth loosening condition;
    a selected one of said tooth engaging portions being removable from said body in a second tooth removal condition; and
    said body having a distal and polygonal cross sectional shaped end, a support pad mounted atop a neck, said neck terminating in an interconnecting base with a through aperture for receiving said second end of said body and in order to engage said support pad to said body in the second condition, said other selected one of said tooth engaging portions being applied against a surface of the tooth concurrent with said pad adapted to being applied to the gum surface such that rotation of said body dislodges the tooth.

\* \* \* \* \*